(12) United States Patent
Holmen et al.

(10) Patent No.: US 8,029,285 B2
(45) Date of Patent: Oct. 4, 2011

(54) IMPLANT, ARRANGEMENT COMPRISING AN IMPLANT, AND METHOD FOR INSERTING SAID IMPLANT IN BONE TISSUE

(75) Inventors: Anders Holmen, Göteborg (SE); Lars Rasmusson, Kullavik (SE); Mats Wendel, Mölnlyeke (SE)

(73) Assignee: Astra Tech AB, Molndal (SE)

( * ) Notice: Subject to any disclaimer, the term of this patent is extended or adjusted under 35 U.S.C. 154(b) by 11 days.

(21) Appl. No.: 10/399,163

(22) PCT Filed: Aug. 14, 2002

(86) PCT No.: PCT/SE02/01458
§ 371 (c)(1),
(2), (4) Date: Apr. 14, 2003

(87) PCT Pub. No.: WO03/015654
PCT Pub. Date: Feb. 27, 2003

(65) Prior Publication Data
US 2004/0006346 A1  Jan. 8, 2004

(30) Foreign Application Priority Data
Aug. 15, 2001 (SE) .................................... 0102749

(51) Int. Cl.
*A61C 8/00* (2006.01)
(52) U.S. Cl. ........................................................ 433/174
(58) Field of Classification Search .................. 433/173, 433/174
See application file for complete search history.

(56) References Cited

U.S. PATENT DOCUMENTS 2,609,604 A  9/1952  Sprague
3,664,540 A  5/1972  Witkin
(Continued)

FOREIGN PATENT DOCUMENTS

DE  41 30 891 A1  3/1992
(Continued)

OTHER PUBLICATIONS

Excerpts from Steri-Oss Manual: Introduction, Table of Contents, pp. 2.3, 2.4 and 2.5.
(Continued)

*Primary Examiner* — Ralph Lewis
(74) *Attorney, Agent, or Firm* — Birch, Stewart, Kolasch & Birch, LLP

(57) ABSTRACT

The present invention relates to a screw implant (1) for insertion into a bore hole (50) arranged in bone tissue, said implant having a cancellous portion (3), and a cortical portion (2) having an axial length such that, when installed in the bore hole (50), the engagement of said cortical portion (2) with the bone tissue will generally be confined to the cortical bone tissue layer (52). Said cortical portion (2) presents an outer surface which is threaded for accomplishing said engagement, and has an outer design such that, when being screwed into said bore hole under action of a screwing torque, said cortical portion (2) acts so as to increase the compression of the cortical bone tissue only, in essentially radial directions of the implant, resulting in a distinct increase of the screwing torque needed for screwing the implant (1). Said increase is usable as an indication that the implant (1) is in place or nearly in place in the bore hole.
The invention also relates to an arrangement comprising an implant and a bore hole, and a method for insertion of an implant into a bore hole.

34 Claims, 6 Drawing Sheets

U.S. PATENT DOCUMENTS

| | | | |
|---|---|---|---|
| 4,547,157 A | 10/1985 | Driskell | |
| 4,723,913 A | 2/1988 | Bergman | |
| 4,826,434 A | 5/1989 | Krueger | |
| 4,932,868 A | 6/1990 | Linkow et al. | |
| 4,988,299 A | 1/1991 | Branemark | |
| 5,000,686 A | 3/1991 | Lazzara et al. | |
| 5,074,790 A | 12/1991 | Bauer | |
| 5,076,788 A | 12/1991 | Niznick | |
| 5,078,607 A | 1/1992 | Niznick | |
| 5,147,363 A | 9/1992 | Harle | |
| 5,259,398 A * | 11/1993 | Vrespa | 128/898 |
| 5,302,126 A | 4/1994 | Wimmer et al. | |
| 5,376,004 A | 12/1994 | Mena | |
| 5,403,136 A * | 4/1995 | Mathys | 411/310 |
| 5,427,527 A | 6/1995 | Niznick et al. | |
| 5,435,723 A | 7/1995 | O'Brien | |
| 5,527,183 A | 6/1996 | O'Brien | |
| 5,571,017 A | 11/1996 | Niznick | |
| 5,588,838 A | 12/1996 | Hansson et al. | |
| 5,601,429 A | 2/1997 | Blacklock | |
| 5,636,989 A * | 6/1997 | Somborac et al. | 433/173 |
| 5,727,943 A | 3/1998 | Beaty et al. | |
| 6,217,331 B1 * | 4/2001 | Rogers et al. | 433/173 |
| 6,220,860 B1 | 4/2001 | Hansson et al. | |
| 6,358,050 B1 * | 3/2002 | Bergstrom et al. | 433/173 |
| 6,547,564 B1 * | 4/2003 | Hansson | 433/174 |
| 6,655,961 B2 * | 12/2003 | Cottrell | 433/173 |
| 6,672,872 B2 * | 1/2004 | Cottrell | 433/173 |
| 6,953,463 B2 * | 10/2005 | West, Jr. | 606/73 |

FOREIGN PATENT DOCUMENTS

| | | |
|---|---|---|
| EP | 0 388 576 A1 | 9/1990 |
| EP | 0 424 734 | 5/1991 |
| FR | 2.095.504 | 2/1972 |
| FR | 2 667 499 A1 | 4/1992 |
| TW | 239291 | 1/1999 |
| WO | WO 83/02555 A1 | 8/1983 |
| WO | WO-93/00518 | 1/1993 |
| WO | WO 94/09717 A1 | 5/1994 |
| WO | WO 94/17750 A1 | 8/1994 |
| WO | WO 95/08963 A1 | 4/1995 |
| WO | WO-97/29713 | 8/1997 |
| WO | WO 00/03657 A1 | 1/2000 |
| WO | WO 00/47127 A1 | 8/2000 |
| WO | WO-01/24737 A1 | 4/2001 |
| WO | WO-01/49199 A2 | 7/2001 |

OTHER PUBLICATIONS

List of publications relating to Steri-Oss Implants.

Implants osteointegres: considerations generales, locales et applications clinques, 1re partie, by Andre P. Saadoun in "Clinic/Odontologia" No. 5/1989.

Implants osteointegres: considerations generales, locales et applications clinques, 2re partie, by Andre P. Saadoun in "Clinic/Odontologia" No. 1/1990.

Production drawing No. DP01-2003-[redacted].

* cited by examiner

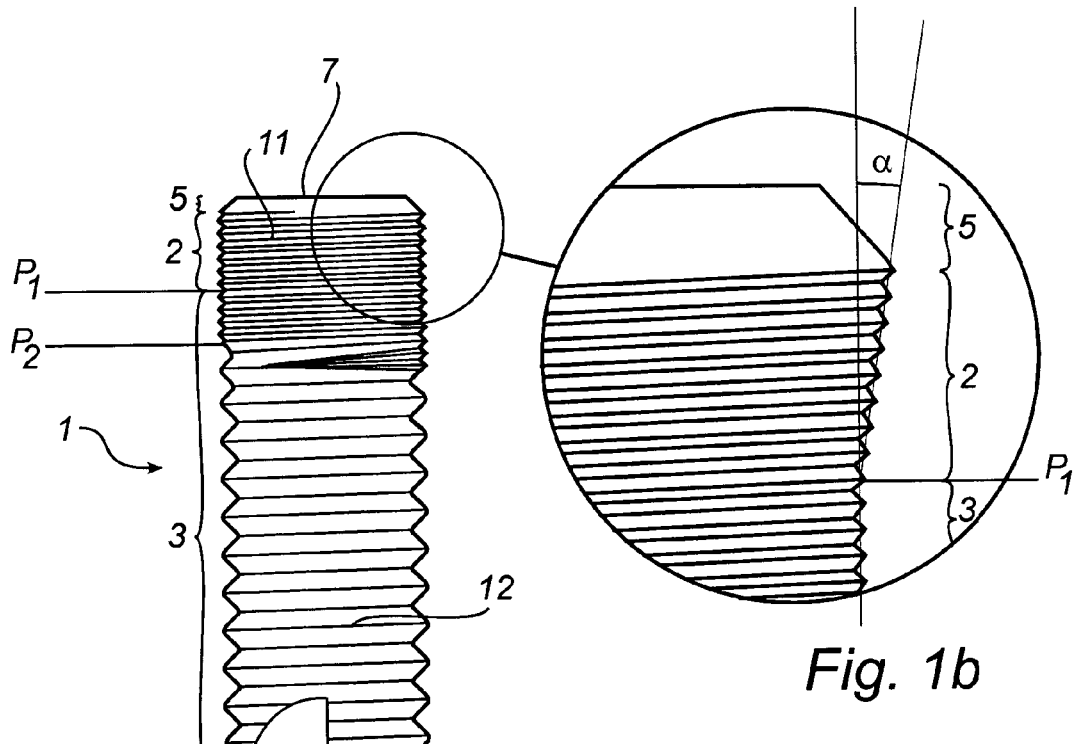
Fig. 1b
Fig. 1a
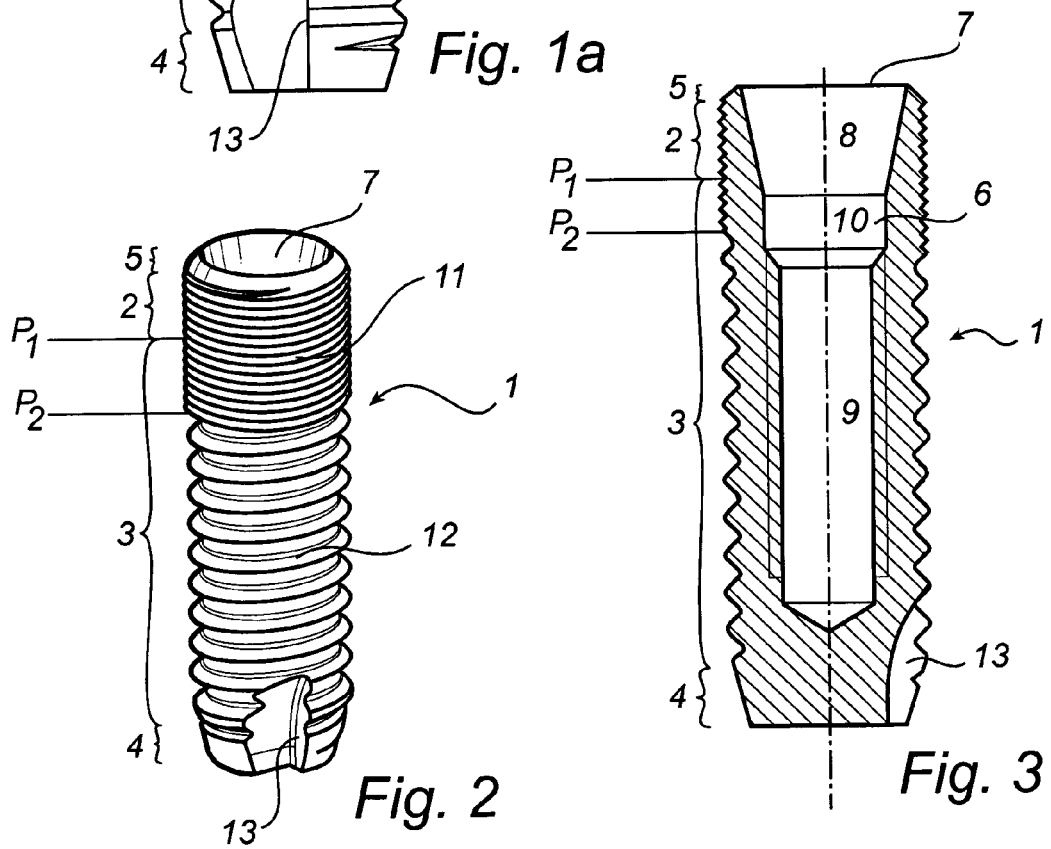
Fig. 2
Fig. 3

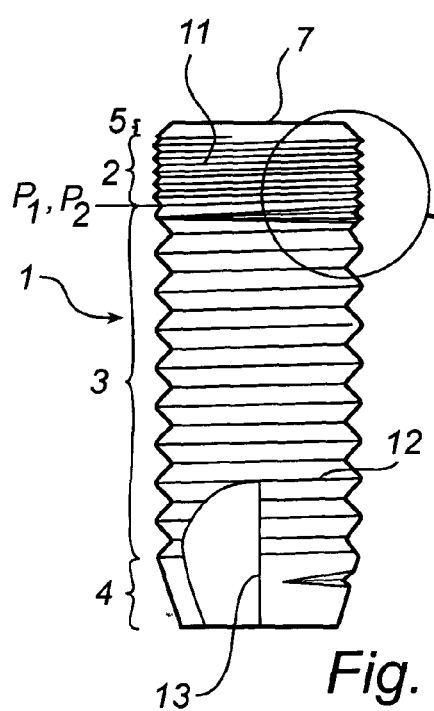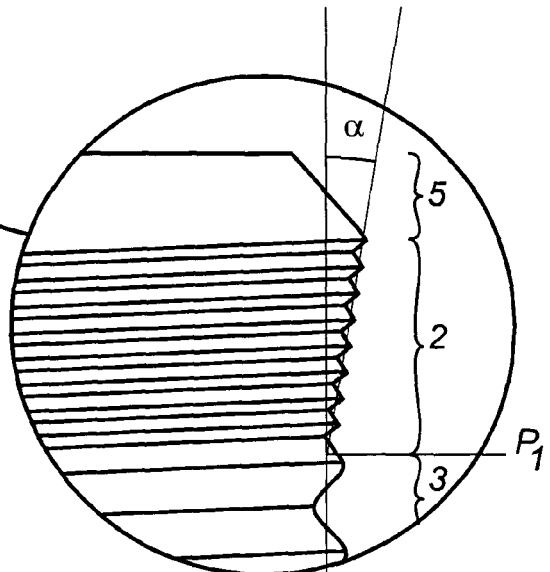
*Fig. 5a*  *Fig. 5b*
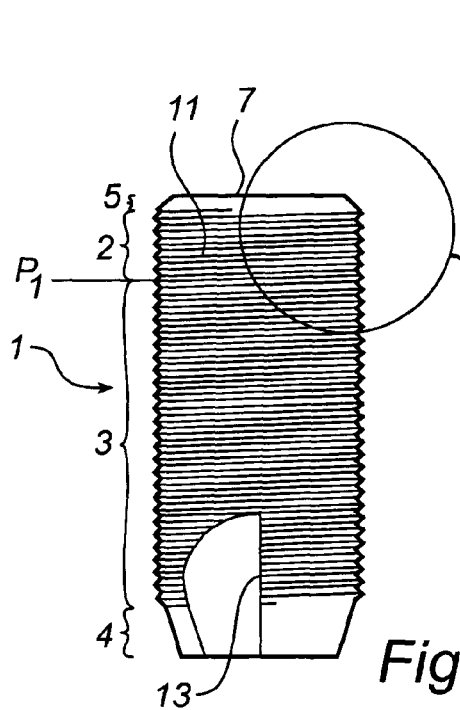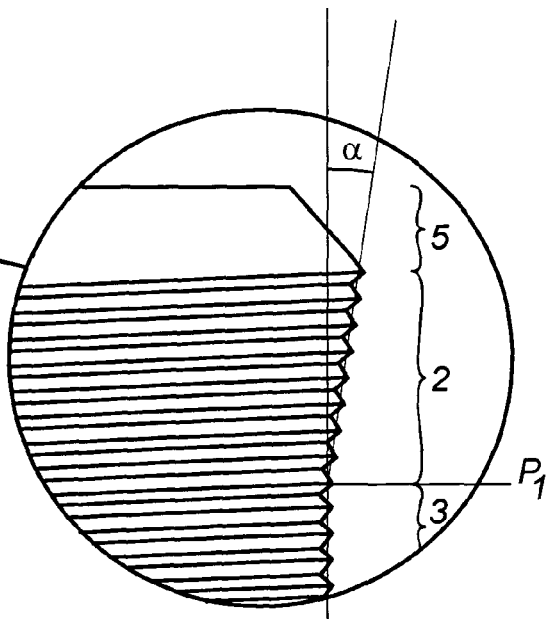
*Fig. 6a*  *Fig. 6b*

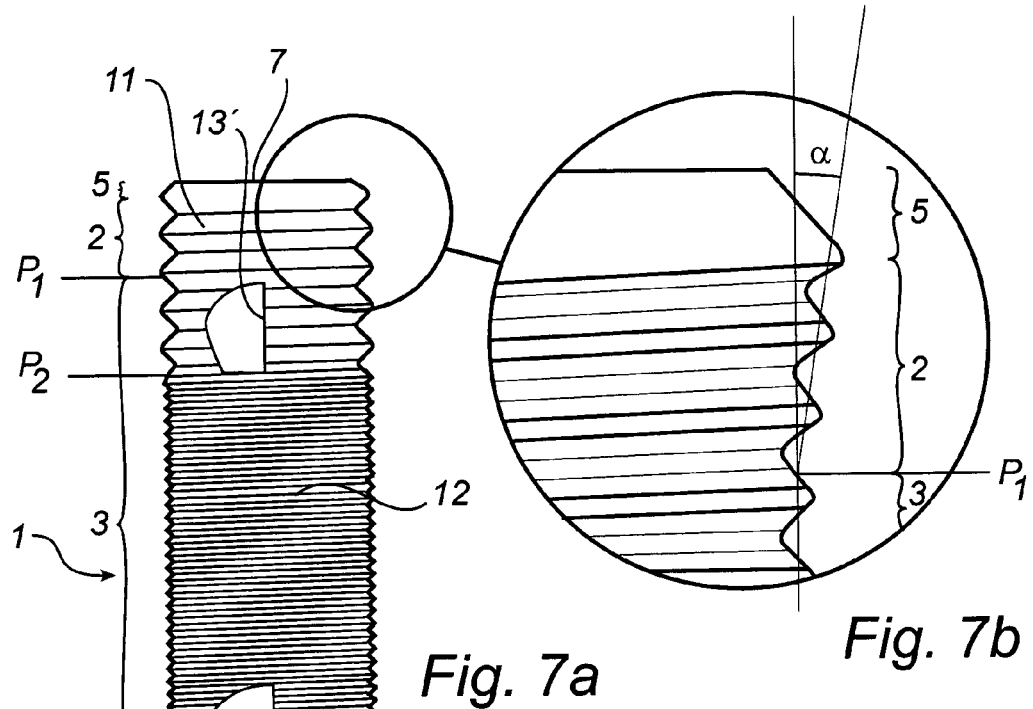
Fig. 7a
Fig. 7b
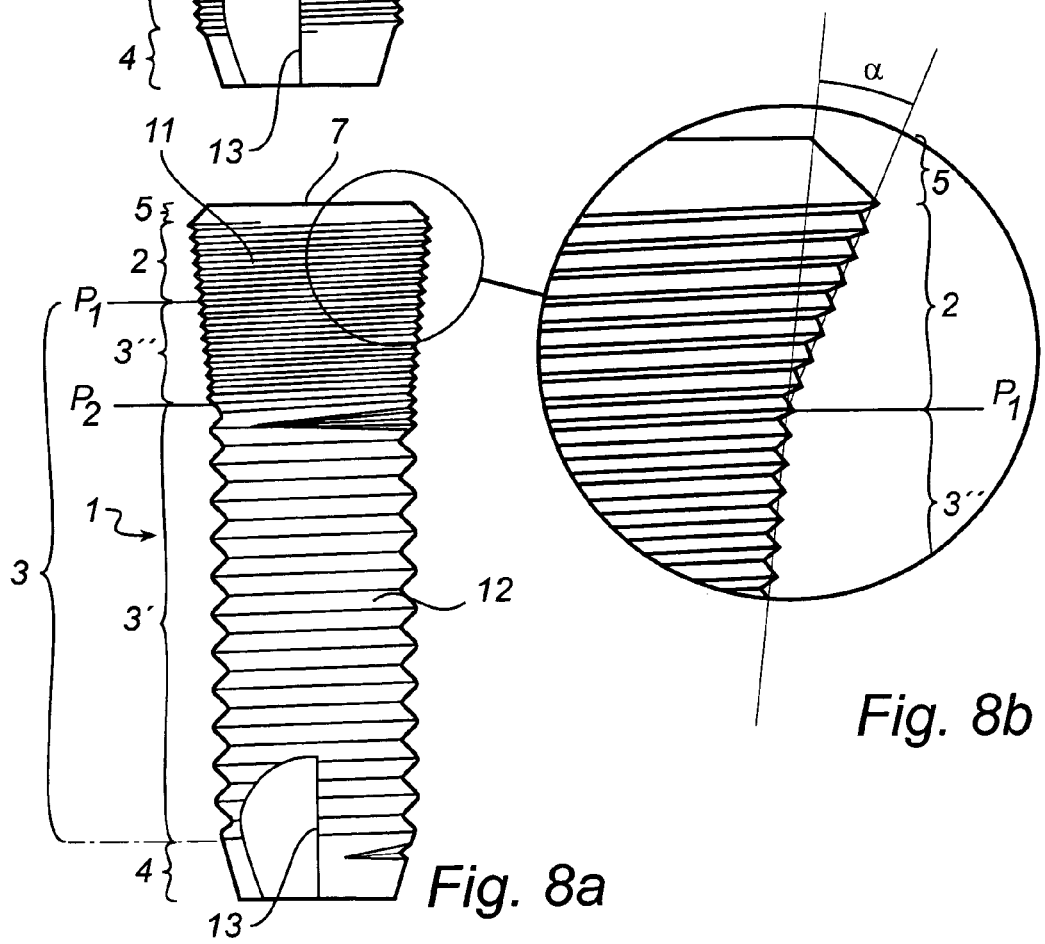
Fig. 8a
Fig. 8b

IMPLANT, ARRANGEMENT COMPRISING AN IMPLANT, AND METHOD FOR INSERTING SAID IMPLANT IN BONE TISSUE

This application is the national phase under 35 U.S.C. §371 of PCT International Application No. PCT/SEO2/01458 which has an International filing date of Aug. 14, 2002, which designated the United States of America.

FIELD OF THE INVENTION

The invention relates to a screw implant for insertion into a bore hole arranged in bone tissue, said implant having a cancellous bone engagement portion, referred to as cancellous portion, and a cortical portion having an axial length such that, when installed in the bore hole, the engagement of said cortical portion with the bone tissue will generally be confined to the cortical bone tissue layer. Said cortical portion presents an outer surface which is threaded for accomplishing said engagement. It further relates to an arrangement for facilitating insertion of a screw implant in bone tissue including a screw implant and a bore hole. The invention also relates to a method of inserting an implant into a bore hole.

BACKGROUND OF THE INVENTION

Screw type implants are implants having outer surfaces being threaded and which are used as anchoring members for different prostheses, such as dental and orthopaedic prostheses. To this end, this type of implant is screwed into a bore hole arranged in the bone tissue of a bone tissue structure at a site where a prosthesis is required. The bore hole may be formed to a shape generally corresponding to the shape of the implant, although slightly smaller in size. These implants may be provided with self-cutting edges, so as to cut one or more internal threads in the inner wall of the bore hole during the screwing in of the implant. If there are no self-cutting edges, the bore must be internally threaded before insertion of the implant.

Bone tissue has two components, cancellous bone tissue and cortical bone tissue. The major part of a bone is normally built up of the cancellous bone tissue, which is a relatively soft tissue in the interior of the bone. The cortical bone tissue is harder and normally forms a relatively thin layer surrounding the cancellous bone. Thus, in their final position, screw implants of the type described would typically be in contact with cancellous bone tissue along a larger part of its length, and with cortical bone tissue only at a shorter portion at one end of the implant.

When a screw type implant is in anchored position in the bone tissue, a superstructure for carrying a prosthetic part may be secured to the implant. In the case when a screw implant will be used to secure a dental prosthesis, the superstructure will typically comprise an abutment or transmucosal component, which engages the implant to bridge the gingiva overlaying the maxilla or mandible at the implant site. The prosthetic part, e.g. a crown, a bridge or a denture is then secured to the abutment. The implant could also be formed integrally with a superstructure, such as a transgingival component, on which for example a crown is directly secured.

A problem occurring when using many prior art screw type implants is referred to as the bone resorption problem. Bone resorption is a term used for a process in which, once an implant is installed in the bone tissue, the bone surrounding the implant tends to degenerate. This is highly undesired, since a diminished amount of bone surrounding the implant will lead to diminished stability and sometimes result in failure of the prosthesis. This is particularly the case because bone resorption primarily occurs in the cortical bone, which, as mentioned above, is the hardest part of the bone. Once bone resorption is a fact, secondary problems may also appear. Such secondary problems, particularly related to dental implants, are for example deposition of plaque, resulting in inflammation in the gingival tissue surrounding the implant, or down-growth of gingival tissue along the exposed end of the implant. Also, the aesthetic appeal of the implant is undermined by bone tissue resorption, which is an important drawback in particular when the implant is intended for dental applications since dental prosthesis form part of the field of cosmetic surgery.

The biological causes of bone resorption are not yet completely understood. According to the inventors' belief, it is however important to ensure proper loading of the implant, since both mechanical over-stimulation and under-stimulation of bone tissue have been seen to cause bone resorption. Prior work by the inventors has been directed towards the issue of developing an implant that transmit the axial loading applied thereupon in an appropriate way to bone. During this work, it has been found to be relevant that the loading is distributed evenly to the adjacent bone tissue, meaning that large stress concentrations or peaks are avoided.

WO 00/03657 (Astra Aktiebolag; Hansson) discloses a prior art screw type implant having a cylindrical shaft, which is adapted in use to be embedded in bone tissue, and which has an outer surface provided with a circumferentially-oriented roughness. The circumferentially-oriented roughness has first and second axial sections with each section comprising a series of circumferentially-oriented peaks which have a crest and which are axially spaced apart by troughs. The axial spacing between the crests of adjacent peaks in the first axial section is less than the axial spacing between the crests of adjacent peaks in the second axial section. The first and second axial sections of circumferentially-oriented roughness are adapted to provide the same or substantially the same pitch. The threads constituting the circumferentially-oriented roughness are self-tapping. Further, the implant as described is to be substantially completely submerged into the bone tissue and the top of the implant is flush with the outer surface of the bone into which it is inserted.

In the above-mentioned implant, the first and second sections of circumferentially-oriented roughness improve the ability of the implant to transmit load evenly to the bone tissue in order to inhibit marginal bone resorption.

A disadvantage with the above-mentioned implant might be revealed when installing it, as is common, into a bore hole. The size of the bore hole should be adapted so that the implant can be screwed into the hole, using its self-tapping cutting edges to cut a thread in the walls of the bore hole. The threads created in that way are useful for holding the implant in place, thus increasing its stability and promoting the healing process. Unfortunately, there is a risk that the surgeon, when having screwed the implant into a position where it has reached the bottom of the bore hole, happens to continue screwing the implant. Naturally, the implant cannot be screwed further into the bone from this position. Instead, the extra screwing merely rotates the implant in the bore hole, while it remains at the same depth, which rotation causes destruction of the previously cut internal threads in the bore hole. Without the internal threads, the stability of the implant is impaired. Less stability leads to longer healing time for the implant, and an increased risk for secondary problems. Such a secondary problem, being particularly problematic in dental applications is the formation of unwanted soft connective tissue around the implant.

U.S. Pat. No. 5,427,527 (Niznick) discloses other prior-art screw type implants. In for example FIG. 1B (showing prior art in relation to the invention of the referenced patent) a cylindrical implant is depicted having a smooth upper portion with an external hexagonal projecting head. The head portion is extending in a radial direction but only to a diameter having about the same size as the outer diameter of the threads of the shaft portion of the implant. Thus, this implant, although it is provided with some kind of head portion, seems to be prone to the same risk of fracturing the threads in the bore hole as the implant in WO 00/03657 (Astra Aktiebolag, Hansson) mentioned above. In the same document, a conical implant is described (FIG. 2). The angle of taper of the implant is preferably between 1° and 3°, and it is mentioned in the text that at least 50% of the implant length should be conical. The implant is to be inserted into a cylindrical bore hole in the bone tissue, being larger in diameter than a lower part of the implant and smaller in diameter than an upper part of the implant. Thus, when the conical implant is screwed into the cylindrical bore hole, the bone is spread about the upper part of the implant, which is supposed to increase the amount of bone to which the implant have contact.

In U.S. Pat. No. 5,427,527 (Niznick), the aim is to provide a conical implant to be used where there is little or so thin bone that narrower implants have previously been used. However, also in this prior art, the surgeon could easily continue to apply a growing torque even after the implant has reached the end of the hole, thus turning it so as to destroy the previously cut threads of the bore hole. Accordingly, this conical implant may be prone to the same problem as described above in relation to the implant of WO 00/03657 (Astra Aktiebolag, Hansson)

Another disadvantage is that the conical shape of the implant causes a large amount of bone to spread and consequently be subjected to extra loading. The idea is that this should increase the stability of the implant. However, the extra loading might over-load the bone tissue, resulting instead in bone resorption and following poor stability of the implant.

SUMMARY OF THE INVENTION

The object of the invention is to provide an implant that, in relation to prior art implants, is easier to install in a correct manner Especially it should diminish the problem of threads being damaged at insertion of the implant. Further, the implant should still be a well functioning implant in other important aspects, such as providing stable primary fixation, initial stability and proper loading of the bone tissue while not being prone to marginal bone resorption.

The above mentioned object is achieved by a screw implant for insertion into a bore hole arranged in bone tissue, said implant having a cancellous portion, and a cortical portion having an axial length such that, when installed in the bore hole, the engagement of said cortical portion with the bone tissue will generally be confined to the cortical bone tissue layer. Said cortical portion presents an outer surface which is threaded for accomplishing said engagement, and has an outer design such that, when being screwed into said bore hole under action of a screwing torque, said cortical portion acts so as to increase the compression of the cortical bone tissue only, in essentially radial directions of the implant, resulting in a distinct increase of the screwing torque needed for screwing the implant, which increase is usable as an indication that the implant is in place or nearly in place in the bore hole.

The term "cortical bone engagement portion" is used to define a portion of the implant that, in an implanted state, would mainly be engaged with the cortical bone tissue layer. For simplicity, the term will hereinafter in the description and in the claims be referred to as "cortical portion". Similarly, the term "cancellous bone engagement portion" will be referred to as "cancellous portion" and refers to a portion of the implant that would mainly be engaged with cancellous bone tissue.

A first general idea of the invention is thus to provide an implant having a cortical portion that, when being screwed into a bore hole under action of a screwing torque, acts so as to increase the compression of the cortical tissue in generally radial directions. The increased compression results in a distinct increase of the screwing torque needed for screwing the implant, said torque forming an indication that the implant is in place or almost in place in the bore hole. Thus, the risk of inadvertent screwing of the implant an extra turn is significantly diminished. In order to obtain said increase of the compression the shape of the bore hole should preferably not follow the outer contour of the cortical portion. For example, if the overall shape of the implant is cylindrical, with a conical cortical portion, the bore hole could be entirely cylindrical. However the bore hole may, as is usual, have a slightly smaller diameter than the cancellous portion.

The outer design of the cortical portion would be such that the outer volume of the cortical portion per length unit of the implant is increased in relation to the outer volume of the cancellous portion per length unit of the implant. It should be noted that already the cancellous portion, will, as it is gradually screwed into the bore hole, compress the cortical tissue somewhat. However, the screwing in of the cortical portion will increase the compression of cortical bone tissue, resulting in the desired increase of torque needed to turn the implant.

The cortical bone tissue is hard enough to provide a perceptible change in screwing torque, even if the compression is only slightly increased. However, the compression must not be unnecessarily large, since there are indications that the cortical bone is sensitive to compression and might be damaged of too high amounts of compression. Thus, the compression used should be a slight compression such that a distinct increase of the screwing torque is achieved while the compression of cortical tissue is held within acceptable levels.

Further, the total compression of bone tissue should be minimised. This is advantageous, since over-compression may lead to bone resorption and weakening of the tissue, leading to diminished initial stability of the implant. As mentioned above, it has been found that a slight increase of the compression of the cortical bone only is sufficient to achieve the desired distinct rise in screwing torque. Thus, there is no need to increase the compression of other parts of the bone tissue. Also, in order to be useful as an indication of the implant being in place or almost in place, the rise in torque should not appear until the final stage of the insertion procedure of the implant, that is, when the cortical portion of the implant is engaging the cortical bone. Accordingly, it is advantageous that the axial length of the cortical portion is such that the engagement of the cortical portion of the invention is generally confined to the cortical tissue layer.

Another advantage resulting from the fact that increase of compression of the cortical bone tissue only is used is that such a compression could be achieved by only a small alteration of the outer shape of a cortical portion of a prior art implant. Thus, the overall shape of the prior-art implant is not significantly changed by the provision of a cortical portion as proposed in the invention. Consequently, advantages or alternatives provided by existing implant shapes are not necessarily affected by the provision of a cortical portion as in the invention upon them. This is particularly important in order to take advantage of previous experiences and designs made to ensure that an even load distribution is obtained around the implant in order to avoid bone resorption.

Another advantage is that the increased compression increases the pressure between the implant and the cortical tissue just after implantation, resulting in more stable primary fixation and increased initial stability of the implant. These factors facilitate the bone tissue formation around the implant, diminish the risk of formation of unwanted soft connective tissue around the implant as well as the risk of bone resorption, and shorten the time for healing.

For accomplishing the engagement of the cortical portion with cortical bone, the cortical portion is provided with a threaded outer surface. With "threaded" is meant a surface allowing the portion to function as a screw. Thus, any surface having a helical arrangement fulfilling this purpose would be confined in the term "threaded", for example a surface having a series of discontinuous protrusions, subsequently following ribs or a conventional thread. At present, a surface presenting a conventional thread seems to be the most advantageous alternative.

The threaded surface is useful in that its engagement with the cortical bone tissue will increase the friction between the cortical bone and the implant, thus contributing to the distinct rise in screwing torque needed when the cortical portion is screwed into the bore hole. Owing to this effect, the compression of cortical bone tissue can be held smaller that what would be necessary if a smooth surface was used, which is advantageous as discussed above. Further, during screwing in of the implant, the threaded surface urges the cortical portion down into the bore hole, compressing the cortical tissue in essentially radial directions. Without the threaded surface, there might be an increased risk that forces from the bone tissue which counteract the screwing in of the cortical portion overcome the forces urging the cortical portion downwardly. In that case, the screwing torque applied to the implant would act only to rotate the implant, but not to advance it in a longitudinal direction, whereby internal threads cut in the bore hole may be damaged.

Another advantage with threaded surfaces is that they have been shown beneficial to bone tissue ingrowth and are useful to enable proper load distribution to the surrounding bone tissue. Due to the load distribution function, they are useful to stimulate bone growth and inhibit marginal bone resorption. Also, the threaded outer surface of the cortical portion will contribute to the primary fixation and initial stability of the implant.

Now returning to the definition of the cortical and cancellous portions of the implant. Normally, an implanted screw implant is in contact with both cancellous bone tissue and cortical bone tissue. However, since the cortical bone tissue constitutes a relatively thin layer around the bone, the major part of the length of a screw implant will be in contact with the cancellous bone. Thus, the length of the cortical portion of an implant will be relatively short in relation to the implant length, as it should largely correspond to the thickness of the cortical bone tissue layer. Said thickness varies with the type of bone, the implantation site, and individually from patient to patient. A normal thickness would be around 0.5-1 mm to 3 mm.

When discussing cortical and cancellous tissue in this application, reference is made to normal cases of bone tissue structures, as described above. There are however unusual cases, where the bone comprises almost only cortical tissue. The unusual cases are the result of a process of transformation of the bone tissue, which might occur in particular regarding the lower jaw of patients that have used loose overdentures for a long time. The implant of the invention is primarily designed to be useful for the normal cases, although it may also function when used for the unusual cases.

Throughout the description and the claims, any reference to directional terms as "up" and "down" and related terms such as top, bottom, below etc referring to the implant should be interpreted as "up" meaning towards the head end or trailing end, i. e. the coronal end of the implant, and "down" meaning towards the insertion end, i. e. the apical end of the implant. Thus the "lower part" of the implant would refer to the part that would first be introduced into a bore hole. Obviously, this does not constitute any restriction regarding in what actual directions the implant may be implanted and used.

The cortical portion of an implant according to the invention would be positioned at the uppermost end of the implant, so as to be in engagement with the cortical bone tissue when the implant is in its final position.

The effect provided by the invention on the screwing torque may be more easily explained if regarding the screwing torque needed to turn an implant as a function of the screwed in length of the implant. Such a function for an implant according to the invention would present a first portion having a first gradient, and a second portion having a second gradient being larger than the first gradient. The first portion would generally correspond to the screwing in of the cancellous portion of the implant according to the invention, while the second portion would correspond to the screwing in of the cortical portion of the implant. The difference in gradient between the first and second portion corresponds to the perceptible rise in screwing torque used as an indication that the implant is or is soon to be in place.

The above object of the invention is further achieved by a generally cylindrical screw implant for insertion into a cylindrical bore hole arranged in bone tissue, said implant having a cancellous portion presenting a cylindrical outer surface, wherein said implant is provided with a cortical portion, having an axial length such that, when installed in the bore hole, the engagement of said cortical portion with the bone tissue will generally be confined to the cortical bone tissue layer, said cortical portion presenting a conical outer surface being threaded for accomplishing said engagement and which has a conical taper such that said conical outer surface forms an angle of less than 5° in relation to the cylindrical outer surface of the cancellous portion.

This aspect of the invention is particularly useful since it regards a generally cylindrical implant, which is the type of implant that have been most prone to inadvertent destruction of the inner threads of the bore hole during installation.

So, there is provided a generally cylindrical screw implant to be inserted into a cylindrical bore hole. According to the prior art, the cylindrical bore hole may have a slightly smaller diameter than the cylindrical implant, such that internal threads may be formed on the inner walls of the hole for engagement with the screw implant. According to the invention, the cylindrical implant is provided with a cortical portion presenting a conical outer surface, forming an angle of less than 5° in relation the cylindrical outer surface of the cancellous portion of the implant. Thus, when screwed into the cylindrical bore hole in the bone, the cortical portion will likewise form an angle of less than 5° in relation to the inner wall of the cylindrical bore hole, and thus compress the cortical bone tissue surrounding it in generally radial directions.

It has surprisingly been found that the minor angle specified above will provide a conicity resulting in a distinct rise in screwing torque being sufficient for the surgeon to feel and appreciate as an indication that the implant is in place or soon to be in place. Nevertheless, the angle is not so large that the cortical portion would harm the cortical bone by compressing it too much. Also, since the axial length of the cortical portion is such that its engagement with bone tissue is generally confined to the cortical tissue layer, there is no unnecessary compression of bone in radial directions around the cancellous portion of the implant.

Another advantage with the specified small angle formed between the cortical portion and the cancellous portion, and thus between the cortical portion and the inner wall of the cylindrical bore hole is that, if such a cortical portion would be provided on a prior art implant, the overall shape of the prior art implant need not to be significally altered. Consequently, advantages or alternatives provided by the prior art implant shape are not necessarily affected. This is particularly important in order to take advantage of previous experiences and designs made to ensure that an even load distribution is obtained around the implant in order to avoid bone resorption.

Regarding the expression "conical" outer surface regarding the cortical portion, it should be understood as a general expression, the said conicity could be achieved by various shapes, such as a regular cone or a funnel-shaped cone or even by a series of discrete steps, as long as the increase in radial extension of each steps is not so large as to risk unwanted compression of the bone in a longitudinal direction. Also, the cortical portion could comprise two or more parts having different conicity. For example, the cortical portion could comprise a lower conical part and an upper conical part, wherein the outer surface of the lower part forms an angle of 1° with the outer surface of the cancellous portion and the outer surface of the second part forms an angle of 2° with the outer surface of the cancellous portion. In that case, both parts of the cortical portion must fulfil the limitation regarding the angle, meaning that the entire outer surface of the cortical portion forms an angle less than 5° in relation to the outer surface of the cancellous portion. In other words, no part of the cortical portion should have an angle in relation to the cancellous portion exceeding 5°.

The angle formed between outer surfaces should be measured from mean values of the surfaces profiles, respectively. For example, if a threaded surface is provided with a screw thread profile having peaks and valleys, the mean value of the surface profile is at half the peak-to-valley height.

The angle that the outer surface of the cortical portion is forming in relation to the outer surface of the cancellous portion is less than 5°, preferably less than 3°. Advantageously, the angle is in the range 0.5 to 5°, preferably 0.5 to 3°, and most preferred in the range 1 to 2°. These small angles have been shown the most useful when it comes to providing the desired perception of a rise in screwing torque, while keeping the compression of the cortical bone tissue within acceptable levels.

The axial length of the cortical portion is selected so that the engagement of the cortical portion with the bone tissue will generally be confined to the cortical bone tissue layer and so that the cortical portion does not compress more tissue than necessary for having the desired increase in screwing torque. A preferred length is less than or equal to 3 mm, most preferably in the range 0.5-1.5 mm.

The amount of compressed bone and the final screwing torque will be dependent on both the angle of the cortical portion and its axial length. By varying those parameters, the way in which the screwing torque increases may be slightly altered. For example, a rather long axial length in combination with a rather small angle would give a relatively gentle increase in screwing torque. A shorter axial length and a larger angle would give a more sudden increase in screwing torque.

In an embodiment of the invention the cancellous portion is also provided with a threaded outer surface that merges with said threaded outer surface of the cortical portion, such that both threaded outer surfaces are engagable in a common inner threaded surface of the bore hole. Thus, it is ensured that the inner threads that are provided in the upper, conical part of the bore hole is maintained during the insertion of the cortical portion, and despite the compression of the cortical bone, those inner threads will still function so as to increase contact between bone tissue and the cortical portion of the implant. Also, they will contribute to urging the cortical portion into the bore hole and thus reduce the risk that the cortical portion acts as a counter element as previously described. Finally, the two threaded surfaces merging with each other ensures a smooth progression of the screwing in of the implant.

In order to further ensure that the threaded surfaces of the cancellous and the cortical portion, respectively, may engage the same inner threads on an inner surface of a bore hole, said threaded surfaces advantageously present the same lead.

The lead of a screw is defined as the distance advanced in a direction parallel to the screw axis when the screw is turned one revolution.

For accomplishing a threaded surface, the surface is provided with at least one threading. A threading is here to be understood as the helical structure allowing the surface to function as a screw, for example the series of discontinuous protrusions, the subsequently following ribs or the conventional thread. Thus, a threaded surface could be provided with one or several threadings. A threading could extend over one or several threaded surfaces. At the time being, the most advantageous threading seems to be a conventional thread.

For example, a first threading may extend along the full axial length of the threaded outer surface of the cortical portion in order to acquire maximal engagement of the cortical portion with the cortical bone tissue.

Also, a threading could extend uninterrupted over both the threaded surface of the cortical portion and at least part of the threaded surface of the cancellous portion. Thus, the above suggestions that the two threaded surfaces should merge with each other and have the same lead are easily realised, in that the two threaded surfaces share the same threading.

The implant could also be provided with two different threadings. For example, the cancellous portion may have a threading being particularly suitable for engagement with cancellous bone tissue, while the cortical portion has a threading being particularly suitable for engagement with cortical bone tissue. Alternatively, the first and second threadings need not to be divided at the very transversal border plane that divides the cortical portion and the cancellous portion. Instead, a first threading may be extending over both the cortical portion and part of the cancellous portion, whereas a second threading extends over the remaining part of the cancellous portion Both single threadings and multiple threadings may be used. A single threading is to be understood as comprising a single helical structure allowing the surface to function as a screw, for example a conventional single thread. A multiple threading comprises at least a first and a second helical structure, the turns of the second helical structure being provided in between the turns of a first helical structure. An example of a multiple threading is a conventional multiple thread.

The multiple threadings are particularly useful when threadings having short axial distance between each thread turn is required. By using multiple threadings, such a short axial distance may be achieved while still having a fair axial lead—that is axial displacement of the implant with each rotation of the implant around its axis. Where a combination of larger and smaller threadings is desired, a combination of single and multiple threadings may be used. For example, the first threading may comprise a multiple threading having a rather small height and axial distance, whereas the second threading comprises a single threading having a larger height and axial distance. Preferably, the first and second threadings are merging so that the multiple threading of the first surface is continuing with the single threading of the second surface. At present, conventional single and multiple threads seem to be the most favourable single and multiple threadings, respectively.

Regarding the details of the threadings, it has been shown that threadings defining a thread height being no greater than 0.20 mm, preferably in the range 0.02-0.15 mm and most preferably 0.05-0.15, are particularly advantageous for engagement with cortical tissue, where their presence seems to diminish the risk of bone resorption. Preferably, the threadings could have a rounded design, so as to avoid any stress peaks that might provoke bone resorption. Advantageously, a rounded thread could have a peak radius around 0.4× a height of the thread, or larger. An example a favourable rounded threading is described in WO 97/29713 (Astra Aktiebolag, Hansson).

Advantageously, the threading may be symmetrical around a longitudinal axis of the implant, in order to provide a lenient introduction of the implant into the bone tissue while taking optimal advantage of the engagement with the inner threads.

According to a further aspect of the invention, there is provided a screw implant for insertion into a bore hole arranged in bone tissue, comprising a lower cylindrical cancellous portion and an upper conical cancellous portion presenting a conical outer surface, wherein said implant is provided with a cortical portion, having an axial length such that, when installed in the bore hole, the engagement of said cortical portion with the bone tissue will generally be confined to the cortical bone tissue layer, said cortical portion presenting a conical outer surface being threaded for accomplishing said engagement and which has a conical taper such that said conical outer surface forms a non-zero angle of less than 5° in relation to the outer surface of the upper, conical part of the cancellous portion.

The idea and function of this aspect of the invention is generally the same as for the generally cylindrical implant according to the invention described above. It will be described in further detail in the specific part of this application.

The invention also relates to a method of installing an implant according to the invention in a bone, comprising the following steps:
  forming in said bone a bore hole having a shape being adapted to the general shape of the implant but being slightly smaller in diameter,
  screwing said implant into the bore hole by applying an insertion torque to the implant until the cortical portion of said implant meets said bore hole, resulting in a distinct rise in the screwing torque needed to turn the implant, which is an indication that the implant is or is soon to be in place.

It is known in prior-art methods to form a bore hole in the bone, corresponding to the general shape of the implant, although slightly smaller in size. The general shape is usually an overall cylindrical or conical shape, but other variants such as combinations of cylindrical and/or conical shapes are also known. Small discrepancies from the general shape are normally not considered when forming the bore hole. In particular, the angle formed by the cortical portion in relation to the cancellous portion of an implant according to the invention is not regarded as part of the general shape of the implant. In fact, the angle between the cortical and the cancellous portion is so small that it would hardly be recognised by the naked eye.

When an implant according to the invention is screwed into the bore, the torque needed for screwing the implant will initially increase slowly, as the cancellous part of the implant is introduced into the bore hole. However, when the cortical portion reaches the bore hole, the torque will rise faster, due to the increasing diameter of the implant. The rise in torque will be felt by the dental surgeon, thus said rise in torque functions as an indicator that the implant should not be screwed any further. Also, the surgeon is assured that the implant is firmly placed in the bone.

In another aspect of the invention, there is provided an arrangement according to the enclosed claims, for facilitating the insertion of a screw implant in a bore hole arranged in bone tissue, comprising a screw implant, having a cancellous portion, and a bore hole having a shape generally corresponding to a shape of the implant.

BRIEF DESCRIPTION OF THE DRAWINGS

By way of example, embodiments of the present invention will now be described with reference to the accompanying figures of drawings in which:

FIG. 1a is a side view of a first embodiment of a dental implant according to the invention;

FIG. 1b shows schematically an enlarged part of FIG. 1a;

FIG. 2 is a perspective view of the dental implant of FIG. 1a;

FIG. 3 is a cross-sectional side view of the dental implant of FIG. 1a;

FIGS. 4a to 4c describe a method of implanting the dental implant of FIG. 1a;

FIG. 5a is a side view of a second embodiment of a dental implant according to the invention;

FIG. 5b shows schematically an enlarged part of FIG. 5a;

FIG. 6a is a side view of a third embodiment of an implant according to the invention FIG. 6b shows schematically an enlarged part of FIG. 6a;

FIG. 7a is a side view of a fourth embodiment of an implant according to the invention FIG. 7b shows schematically an enlarged part of FIG. 7a;

FIG. 8a is a side view of a fifth embodiment of an implant according to the invention FIG. 8b shows schematically an enlarged part of FIG. 8a;

FIGS. 9a to 9c describe a method of implanting the dental implant of FIG. 8a;

DESCRIPTION OF EXEMPLARY EMBODIMENTS OF THE INVENTION

Figure 4A:
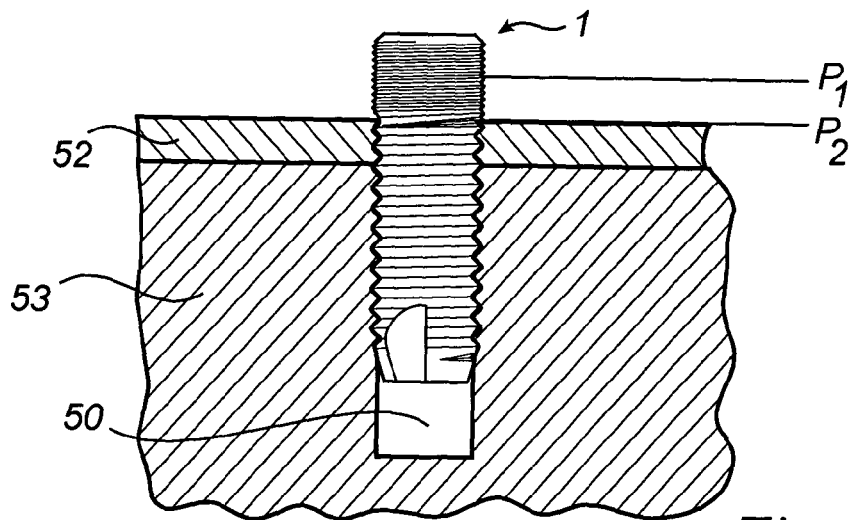

Regarding the figures of drawings, it should be noted that the enlarged portions illustrated in FIGS. 1b, 5b, 6b, 7b and 8b are schematical and inserted for the purpose of better describing features that would not be visible to the naked eye on a correctly scaled drawing. Like features have been provided with like reference numerals in the different figures.

A first embodiment of the invention will now be described in relation to FIGS. 1 to 3. This embodiment shows the inventive concept applied on the previously mentioned prior-art implant as is described in WO 00/03657 (Astra Aktiebolag, Hansson), where it is believed to have a particularly advantageous effect.

The implant 1 having a generally cylindrical shape is a dental implant for insertion into a bore hole drilled in the bone tissue of a maxilla or mandible, for anchorage of a prosthesis. The implant 1 is made from commercially pure titanium, a titanium alloy, another biocompatible metal or metal alloy or a ceramic to promote osseointegration of the implant with the bone tissue of the boundary walls of the bore hole.

The length of the implant 1 is preferably between 8-19 mm and the maximum width around 3-4 mm. The implant 1 depicted in FIGS. 1a to 3 has a length of 12 mm, and a width of 4 mm.

The implant has a cancellous portion 3 presenting a cylindrical outer surface, and a cortical portion 2 having an axial length of 1.5 mm so as to, when installed in a bore hole in bone tissue, generally engage the cortical bone tissue layer. The outer surface of the cortical portion 2 is threaded and has a slight conical taper, so as to form an angle α of less than 5°, in this case 1° with the cancellous portion 3 of the implant (see FIG. 1b). A transversal border plane between the cortical portion 2 and the cancellous portion 3 is referred to as P1.

Below the cancellous portion 3 there is a tip portion 4 being conical, as is known in the art, in order to facilitate the insertion of the implant 1 into the bore hole. The uppermost section 5 of the implant 1 is smooth and cone shaped with its smaller diameter directed towards the top of the implant. The axial extent of the uppermost section 5 is preferably small compared to the total length of the implant 1, as an example no more than 4%, perhaps in the range 1.5%-3.7%. When in place in a bone, the uppermost section 5 is the only part of the implant that is accessible from outside of the bone.

Turning now to FIGS. 2 and 3, the implant is provided with a socket 6 having an open end 7 in the uppermost portion 5 for receiving an abutment structure (not shown), which will bridge the gingiva overlying the bore hole and support/present the prosthetic part. The socket 6 comprises of a conical upper section 8, an internally threaded lower section 9 and a cylindrical intermediate section 10. The abutment structure will have a lower section, which is capable to be screw retained in the implant socket 6 for releasably securing the abutment structure to the implant 1.

The outer surface of the implant 1 is provided with first and second threadings 11 and 12, respectively. A transversal border plane between the first and the second threading 11 and 12 is referred to as P2. The first threading 11 is extending over the cortical portion 2 and part of the cancellous portion 3. The threading 11 thus continues undisrupted from the cancellous portion 3 to the cortical portion 2. Further, the threading 11 is in this case a multiple thread, namely a triple thread, having a height no greater than 0.2 mm, preferably 0.1 mm. Threads with such small heights are sometimes called "micro-threads" and have been shown to be particularly advantageous when provided on the upper part of dental implants, where their presence inhibit marginal bone resorption. Threads having a height greater than 0.2 mm would then be called "macro-threads".

The second threading 12 is provided on the lower part of the cancellous portion 3, and on the tip portion 4. This second threading is in this case a single threading, having a conventional thread with a height being larger than 0.2 mm, in this case 0.3 mm.

The second threading 12 merges into the first threading 11 in that the thread spiral of the single screw thread of the second threading 12 continues with the thread spiral of the triple screw thread of the first threading 11. In this embodiment, the first and second threadings 11 and 12 also have the same lead.

The facts that the first and second threadings 11 and 12 are merging into each other, and have the same lead, and the first threading 11 is continuing uninterrupted across a border plane P1 between the cancellous portion 3 and the cortical portion 2, all contribute to that the implant may be screwed into a bore hole with optimal engagement in and minimal destruction of the internal threads. This is particularly advantageous in combination with the conical cortical portion 2, since the ability of the internal threads cut in the bore in bone tissue of cooperating with the threaded surfaces so as to urge the cortical portion 2 into the bore hole is improved.

As seen in FIG. 1a, the implant 1 has cutting recesses or grooves 13 circumferentially distributed about the circumference of the lower end of the implant 1 for self-tapping of the implant 1 when being screwed into the bore hole. If the implant 1 is not provided with cutting recesses 13, the bore hole may be internally threaded before the implant is inserted.

As should already be clear from the above paragraphs, a border plane P2 between the first and second threadings 11 and 12 is provided below a border plane P1 between the cylindrical cancellous portion 3 and the conical cortical portion 2. In other embodiments of the invention, the two border planes P1, P2 might coincide.

Advantageously, the multiple and single threads of the first and second threadings 11 and 12, respectively, have a rounded design so as to avoid stress peaks in surrounding bone tissue.

Figure 4B:
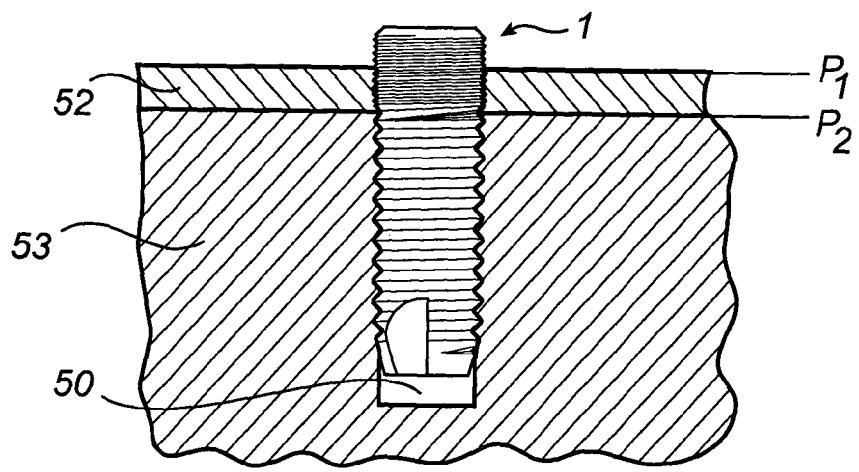
Figure 4C:
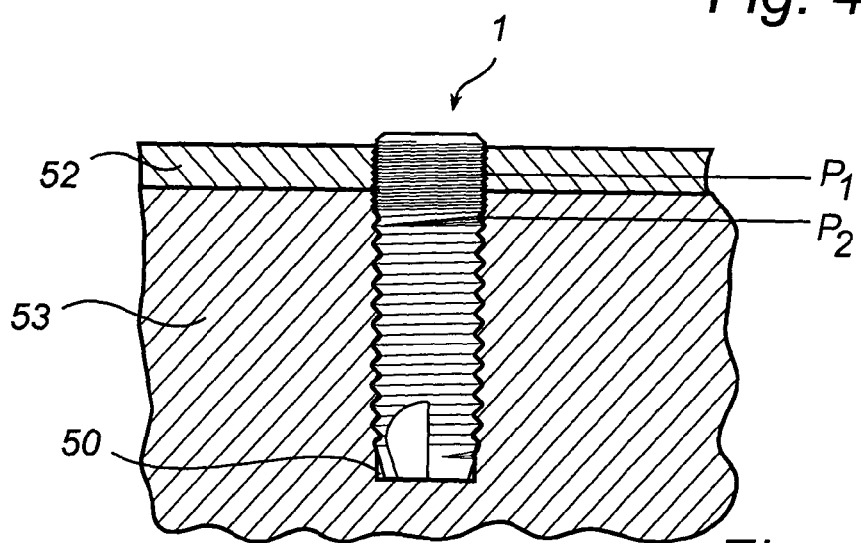

Reference is now being made to FIGS. 4a to 4c, illustrating a method for inserting the implant 1. The implant 1 is screwed into a bore hole 50 provided in bone tissue, comprising a cortical bone tissue layer 52 and a cancellous bone tissue layer 53. The bore hole 50 will, as is known in the art, be shaped so as to correspond to the overall shape of the implant 1, though slightly smaller in size, so that the cutting recesses 13 provided on the implant will tap internal threads in the internal walls of the hole 50. In this context it should be mentioned that the bore hole 50 should not be formed taking the conical cortical portion 2 into account. The bore hole 50 is cylindrical with a diameter somewhat smaller than the diameter of the peaks of the threads of the cancellous portion 3 of the implant 1.

When screwed into the hole 50, the tip portion 4 with the cutting recesses 13 will first be introduced. The torque needed for screwing the implant will increase only very slowly as the implant is successively lowered into the bone (see FIG. 4a). The increase in torque at this stage is primarily due to the increasing area of the implant coming in contact with and tapping the walls of the bore hole 50, which increases the total amount of friction between the implant and the walls. When the border plane P1 between the cancellous portion 3 and the cortical portion 2, coincides with the outer surface of the cortical tissue layer 52, as seen in FIG. 4b, the next few turns of the implant will result in the conical cortical portion 2 being urged down into the hole 50. The compression of cortical bone tissue 52 surrounding the bore hole is then increased and the friction between the inner walls of the bore hole 50 and the cortical portion 2 thus increases distinctly. The distinct rise in torque needed for screwing the implant is perceptible as an indication that the implant is in place, or nearly in place. Also, the compression exerted on the cortical tissue ensures that the implant 1 acquires a good initial stability. Due to the specific design of the cortical portion 2, there is however be no risk that the bone tissue is unnecessary compressed, as has been discussed above.

FIG. 4c shows the implant 1 in its final position in the bone. It should be noted that the cortical portion 2 of the implant 1 is in contact only with cortical bone tissue 52, whereas the cancellous portion 3 is in contact with mainly cancellous tissue 53, but also some cortical tissue 52.

Because of the micro-threads being provided as the first threading 11, the implant 1 is capable of transferring loads evenly to the bone tissue adjacent to the implant 1 and consequently promotes good remodelling of the bone tissue into apposition with the implant 1.

Figure 10:
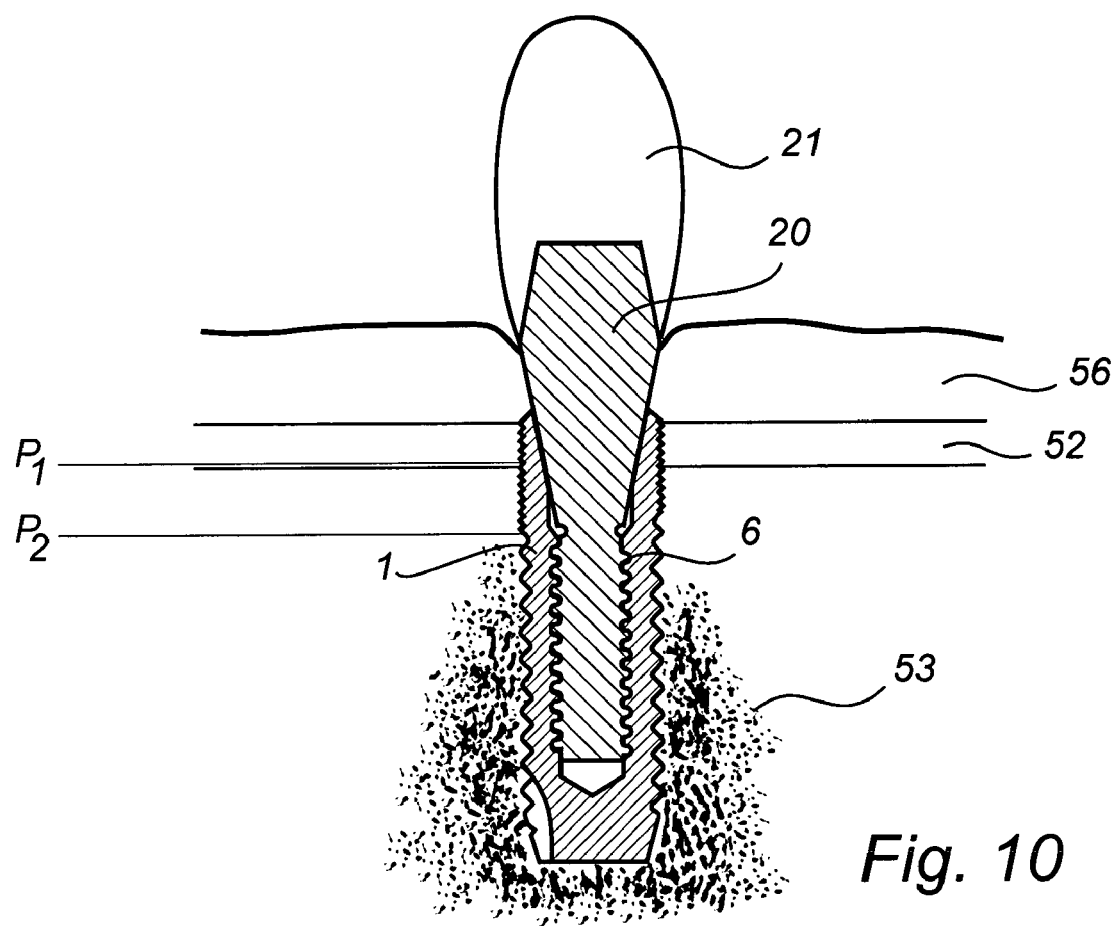
FIG. 10 is a cross-sectional side view of the dental implant of FIG. 1a, when in implanted state and provided with a superstructure on which a dental crown is built.

Finally, in FIG. 10, the implant 1 is depicted when implanted in the bone tissue. An abutment 20 is arranged in the internal socket 6 of the implant. The abutment 20 bridges the gingival tissue 56 that is present above the cortical bone tissue 52. A dental prosthesis 21 is built up on the abutment 20, so as to replace a missing tooth.

In FIGS. 5a and 5b a second embodiment of the invention is shown. This implant is a variant of the implant described in connection to FIGS. 1 to 3. The implant depicted in FIGS. 5a and 5b differs from the implant of FIG. 1 in that only the cortical portion 2 is provided with microthreads, whereas all lower parts of the implant are provided with macrothreads. In other words, the border plane P2 between the first and second threadings 11 and 12 coincides with the border plane P1 between the cortical portion 2 and the cancellous portion 3.

The first threading 11 merges with the second threading 12 in the same manner as described in relation to the first embodiment. Thus, also in this embodiment the threaded outer surface of the cortical portion 2 engages in the same internal threads as the cancellous portion 3, facilitating the insertion of the cortical portion 2 in the bore hole.

In FIGS. 6a and 6b a third embodiment of the invention is shown. This implant is yet another variant of the implant described in connection to FIGS. 1 to 3, differing from the implant in FIG. 1 in that there is only one threading 11 provided on the implant.

The threading 11 extends with no interruption over the tip portion 4, the cancellous portion 3, and the cortical portion 2. In this case, the threading 11 has a triple micro-thread. The micro-thread is believed to contribute to a favourable load distribution around the implant, in particular for inhibiting bone resorption.

In FIGS. 7a and 7b a fourth embodiment of the invention is shown. This implant is yet another variant of the implant described in connection to FIGS. 1a-3. In this embodiment, there are a first threading 11 of the implant that is provided with macro-threads, and a second threading 12 that is provided with micro-threads. In contrast to the embodiment shown in FIG. 1, here, the macro-threads are provided on the cortical portion 2 of the implant and extending partly down the cancellous portion 3. The second threading 12 having the micro-threads is provided on part of the cancellous portion 3. Both of the threadings 11 and 12 are provided with self-tapping cutting edges 13 and 13', respectively. This is because the internal thread cut by the self-tapping micro-threads 13 of the second threading 12 is too small for the macro-threads of the first threaded surface 11. Naturally, the first and second threading 11, 12 need in this case not to merge with each other since they anyway will not engage the same internal threading.

The threaded surface of the cortical portion 2 is however merging with a threaded surface of the cancellous portion 3, since the first threading 11 is extending over both the threaded surface of the cortical portion 2 and part of the threaded surface of the cancellous portion 3. Thus the cortical portion 2 may be smoothly urged into the internal threading cut by self-tapping edges 13' or the first threaded surface 11.

In FIGS. 8a and 8b a fifth embodiment of the invention is depicted. In this embodiment, another prior art implant of the inventors, which is described in WO94/090717 (Astra Aktiebolag, Hansson), is modified according to the invention. The prior art implant of WO94/090717 (Astra Aktiebolag, Hansson) is a fixture for use in a dental implant system, having a lower cylindrical portion and an upper conically flaring portion. The conically flaring upper portion is provided with a circumferentially oriented, defined micro-roughness. The major advantage with the prior art implant is that it has been found not to be subject to marginal bone resorption. This favourable effect is believed to be due to the specific force distribution from the implant to the surrounding bone tissue, which distribution is achieved by the geometry and microroughness of the implant.

The conical part of the prior art fixture makes up a large part of the overall length of the implant, and will clearly be in contact with cancellous bone. Also, the angle of taper of the conical part is rather large. The prior art fixture, having such a large angle of taper, is intended to be inserted into a specifically shaped bore hole in the jaw, having a lower cylindrical part and an upper conical part, corresponding to the shape of the fixture. (See FIGS. 9a-9e) Thus, the above-mentioned problems regarding the possibility of rotating the fixture in the bore hole may be present also with this prior art implant.

In order to eliminate this problem, and to improve initial stability of the implant, according to the invention, a cortical portion is provided, forming a non-zero angle $\alpha$ of less than 5° with respect to the conically flaring surface of the implant.

With reference to FIGS. 8a and 8b, the resulting implant according to the invention will now be described with the terms of this application. A screw implant 1 is provided, comprising a cancellous portion 3 having a lower cylindrical cancellous portion 3' and an upper conical cancellous portion 3" presenting a conical outer surface. The implant 1 is provided with a cortical portion 2, having an axial length such that, when installed in the bore hole, the engagement of said cortical portion with the bone tissue will generally be confined to the cortical bone tissue layer.

The cortical portion 2 presents a conical outer surface being threaded for accomplishing said engagement and which has a conical taper such that said conical outer surface forms a non-zero angle $\alpha$ of less than 5° in relation to the outer surface of the conical cancellous portion 3".

A first threading 11 is extending uninterrupted over both the cortical portion 2 and the conical cancellous portion 3". Thus smooth transition between the conical cancellous portion 3" and the cortical portion 2 is ensured, as discussed in relation to previous embodiments. In this case, the first threading 11 comprises a micro-thread, which is particularly favourable for inhibiting bone resorption. The lower, cylindrical cancellous portion 3' is provided with a second threading 12, in this case a macro-thread. The second threading 12 and the first threading 11 is in this case not merging with each other. Considering the shape of the bore hole, (FIGS. 9a to 9c) the reason why is understood. The cylindrical portion 3' will never come into contact with the inner walls of the upper, conical part of the bore hole, why there is no need to adapt the threadings of the cylindrical cancellous portion 3' and the conical cancellous portion 3" to each other.

The function of the cortical portion 2 will be essentially the same as in the previously described embodiments of the invention. By applying the cortical portion 2 as shown in FIG. 8a to a prior art implant of WO94/090717 (Astra Aktiebolag, Hansson), the advantages of the prior art implant regarding bone resorption can be largely maintained, while adding the advantages of the invention, such as improved initial stability and facilitated placement of the implant.

Figure 9A:
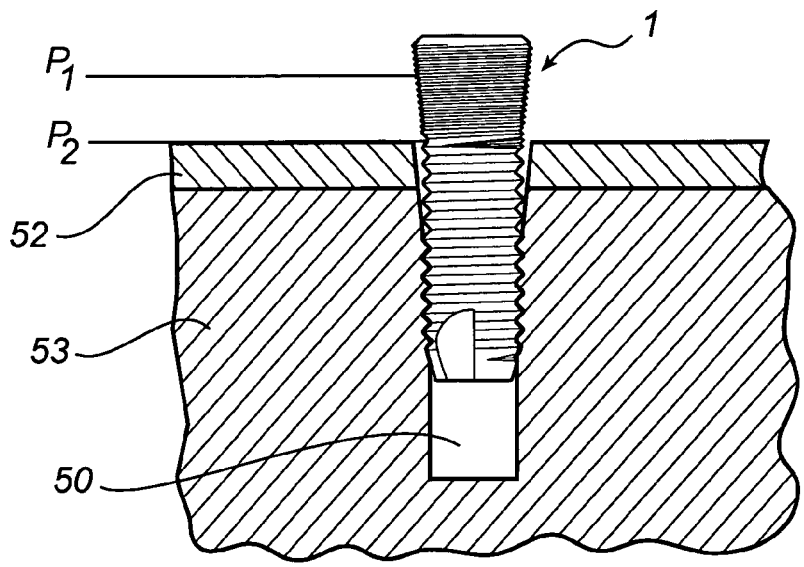
Figure 9B:
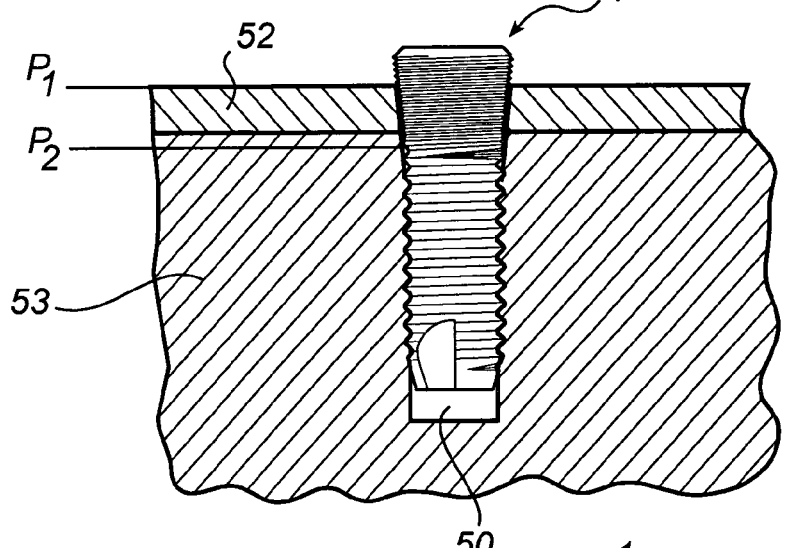
Figure 9C:
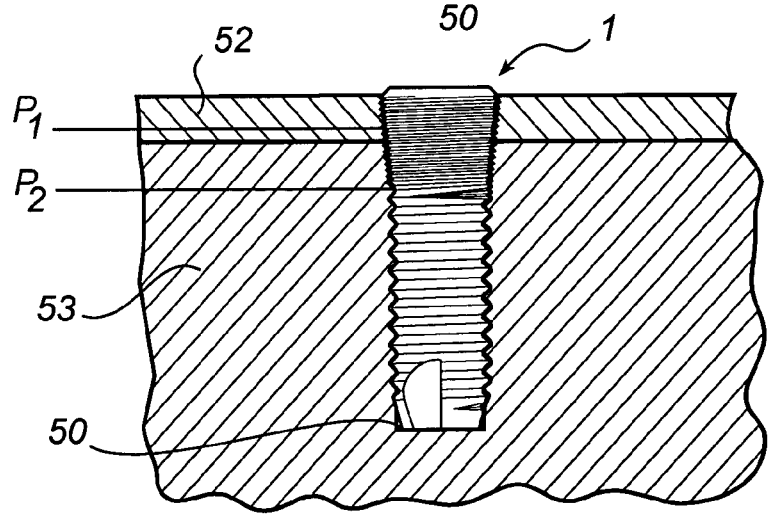

Reference is now made to FIGS. 9a to 9c, illustrating a method for implanting an implant according to this fifth embodiment. A bore hole 50 is provided in the maxilla or mandible of a patient. The bore hole 50 will, as is known in the art, be shaped so as to correspond to the overall shape of the implant, though slightly smaller in size, so that the cutting recesses 13 provided on the implant will function for self-tapping. Thus, the lower part of the bore hole 50 would in this case be cylindrical, whereas the upper part would be conical, and flaring outwardly with an angle corresponding to the cone angle of the conical cancellous portion 3". The bore hole 50 should not be formed taking the cortical portion 2 of the implant into account.

When screwed into the hole 50, the lower, cylindrical cancellous portion 3' with the cutting recesses 13 will first be introduced into the lower cylindrical part of the bore hole. The torque needed for screwing the implant will increase only very slowly as the cylindrical cancellous portion 3' successively engages a larger area of the inner walls of the bore hole 50 (see FIG. 9a). The increase in torque at this stage is primarily due to this increasing area, which increases the total amount of friction. The conical cancellous portion 3" will not engage the outer walls of the upper part of the bore hole until at a later stage in the insertion process. However, when the implant 1 is submerged to the transversal border plane P1 between the conical cancellous portion 3" and the cortical portion 2, as seen in FIG. 9b, the next few turns of the implant will result in the cortical portion 2 being forced down into the conical part of the hole 50. The friction between the walls of the conical part of the bore hole 50 and the cortical portion 2 of the jaw thus increases. The resulting distinct rise in torque needed for screwing the implant 1 is large enough to be perceived by the dental surgeon carrying out the insertion operation. From this indication, the dental surgeon knows that the implant is in place, will soon to be in place, and should not be screwed any further. Also, the surgeon is assured that the implant has acquired a good initial stability by the strong holding forces acting around the cortical portion 2 of the implant 1, due to the slight compression of cortical bone tissue 52.

The implant 1 in place in the jawbone is shown in FIG. 9c. It should be noted that the cortical portion 2 of the implant 1 is in contact with cortical bone tissue 52 only.

To conclude, a dental implant according to the invention has a cortical portion which acts so as to slightly compress the cortical bone tissue so as to
i) give the dental surgeon an indication that the implant should not be screwed further or should only be screwed a little further in a bore hole and
ii) promote the short- and long-term stability of the implant in the bone tissue.

It will be appreciated that the invention has been illustrated with reference to exemplary embodiments and that the invention can be varied in many different ways within the scope of the appended claims. As an example, although the illustrated examples are dental implants, the invention has equal application in other areas, for example, in the orthopaedic area. Further, the features of the implant could be varied. For example, instead of threads other means could be used such as a line of beads or subsequently following protrusions. The shape of the cortical portion may be varied as mentioned above. Also, the implant could be formed integrally with an abutment or spacer portion.

Finally, it is to be noted that the inclusion in the appended claims of reference numerals used in the figures of drawings is purely for illustrative purposes and not to be construed as having a limiting effect on the scope of the claims.

The invention claimed is:

1. A screw-type dental implant for insertion into a bore hole arranged in a human jaw bone, said dental implant comprising:
 a cancellous portion presenting an outer surface which has an apical part with a macro threading and a coronal part with a micro threading, and
 a cortical portion having an axial length such that, when installed in the bore hole, the engagement of said cortical portion with the jaw bone will generally be confined to the cortical bone tissue layer, said cortical portion presenting a conical outer surface which has a micro threading for accomplishing said engagement and which has a conical taper such that said conical outer surface forms, at a transversal border plane between said conical outer surface of the cortical portion and said outer surface of the cancellous portion, a non-zero angle of less than 5° in relation to the outer surface of the cancellous portion,
 wherein the micro threading of the cortical portion and the micro threading of the coronal part of the cancellous portion meet at the transversal border plane, the micro threading of the cortical portion continues uninterrupted across the transversal border plane and a maximum diameter of the dental implant is located in the cortical portion.

2. The screw-type dental implant according to claim 1, wherein the cortical portion has the shape of a truncated regular cone.

3. The screw-type dental implant according to claim 1, wherein said angle is in the range 0.5 to 5°.

4. The screw-type dental implant according to claim 1, wherein said angle is less than less than 3°.

5. The screw-type dental implant according to claim 1, wherein said angle is in the range 0.5 to 3°.

6. The screw-type dental implant according to claim 1, wherein said angle is in the range 1 to 2°.

7. The screw-type dental implant according to claim 1, wherein the axial length of the cortical portion is equal to 3 mm.

8. The screw-type dental implant according to claim 1, wherein the axial length of the cortical portion is less than 3 mm.

9. The screw-type dental implant according to claim 1, wherein the axial length of the cortical portion is in the range 0.5 to 1.5 mm.

10. The screw-type dental implant according to claim 1, wherein the full axial length of the cortical portion is provided with said threading.

11. The screw-type dental implant according to claim 10, wherein said threading is a single threading.

12. The screw-type dental implant according to claim 10, wherein said threading is a multiple threading.

13. The screw-type dental implant according to claim 10, wherein said threading comprises a screw thread.

14. The screw-type dental implant according to claim 10, wherein said threading is defining a thread height being no greater than 0.20 mm.

15. The screw-type dental implant according to claim 10, wherein said threading is defining a thread height in the range 0.02 to 0.15 mm.

16. The screw-type dental implant according to claim 10, wherein said threading has a rounded outer design.

17. The screw-type dental implant according to claim 10, wherein said threading is symmetrical.

18. The screw-type dental implant according to claim 10, further being provided with a second threading.

19. The screw-type dental implant according to claim 18, wherein a transversal border plane between the first and second threadings is provided below said transversal border plane between the cortical portion and the cancellous portion.

20. The screw-type dental implant according to claim 18, wherein a transversal border plane between the first and second threadings is coinciding with said transversal border plane between the cortical portion and the cancellous portion.

21. The screw-type dental implant according to claim 1, wherein the cortical portion is adapted to hold a superstructure.

22. The screw-type dental implant according to claim 21, wherein a blind bore extends into the dental implant from an uppermost end of the cortical portion for holding said superstructure.

23. The screw-type dental implant according to claim 22, wherein said blind bore is internally threaded.

24. The screw-type dental implant according to claim 1, wherein the dental implant is formed integrally with a superstructure provided coronally of said cortical portion, said superstructure protruding from the bone tissue when the dental implant is in its implanted state.

25. The screw-type dental implant according to claim 1, wherein said axial length of the cortical portion is relatively short in relation to the axial length of said cancellous portion.

26. The screw-type dental implant according to claim 1, wherein said cortical portion, when being screwed into said bore hole, acts so as to slightly compress cortical bone tissue in essentially radial directions of the cortical portion.

27. A method of installing the screw-type dental implant according to claim 1 in a jaw bone, comprising the following steps:
   forming in said jaw bone a bore hole having a shape being adapted to the general shape of the dental implant but being smaller in diameter,
   screwing said dental implant into the bore hole by applying an insertion torque to the dental implant until the cortical portion of said dental implant meets said bore hole resulting in a distinct rise in the torque needed to turn the dental implant, which is an indication that the dental implant is or is soon to be in place.

28. The method according to claim 27, wherein an outer part of said bore hole is formed so as to correspond to the cancellous portion of the dental implant.

29. The method according to any of the claim 27 or 28, wherein said bore hole is cylindrical.

30. The method according to claim 27, wherein said bore hole is slightly smaller in diameter than the dental implant.

31. A generally cylindrical screw-type dental implant for insertion into a cylindrical bore hole arranged in a human jaw bone, said dental implant comprising:
   a cancellous portion presenting a cylindrical outer surface and has an apical part with a macro threading and a coronal part with a micro threading, and
   a cortical portion having an axial length such that, when installed in the bore hole, the engagement of said cortical portion with the jaw bone will generally be confined to the cortical bone tissue layer, said cortical portion presenting a conical outer surface which has a micro threading for accomplishing said engagement and which has a conical taper such that said conical outer surface forms, at a transversal border plane between said conical outer surface of the cortical portion and said cylindrical outer surface of the cancellous portion, a non-zero angle of less than 5° in relation to the cylindrical outer surface of the cancellous portion,
   wherein the micro threading of the cortical portion and micro threading of the coronal part of the cancellous portion meet at the transversal border plane, the micro threading of the cortical portion continues uninterrupted across the transversal border plane and a maximum diameter of the dental implant is located in the cortical portion.

32. The screw-type dental implant according to any of claims 1-31, wherein said cancellous portion includes a generally cylindrical portion and a conical portion having a conical taper, said cortical portion includes a conical portion having a conical taper, and said conical taper of the conical portion of said cortical portion is greater than the conical taper of the conical portion of the cancellous portion.

33. A screw-type dental implant for insertion into a bore hole arranged in a human jaw bone, comprising:
   a cancellous portion having a lower cylindrical cancellous portion and an upper conical cancellous portion presenting a conical outer surface, the cancellous portion having a threading, and
   a cortical portion having an axial length such that, when installed in the bore hole, the engagement of said cortical portion with the jaw bone will generally be confined to the cortical bone tissue layer, said cortical portion presenting a conical outer surface which has a threading for accomplishing said engagement and which has a conical taper such that said conical outer surface forms, at a transversal border plane between said conical outer surface of the cortical portion and said conical outer surface of the upper cancellous portion, a non-zero angle of less than 5° in relation to the outer surface of the upper conical cancellous portion,
   wherein the threading of the cortical portion and threading of the cancellous portion meet at the transversal border plane, the threading of the cortical portion continues uninterrupted across the transversal border plane, and the height from thread trough to thread peak over the threaded surface of the cortical portion and over at least part of the threaded surface of the cancellous portion is the same, and a maximum diameter of the dental implant is located in the cortical portion.

34. The screw-type dental implant according to any of claims 1-33, wherein a length of the cortical portion is 7.89% to 18.75% of a total length of the implant.

* * * * *